United States Patent
Cheng et al.

(10) Patent No.: US 9,518,217 B2
(45) Date of Patent: Dec. 13, 2016

(54) TRANSITION METAL CARBENE COMPLEXES AND THE ELECTROLUMINESCENT APPLICATION THEREOF

(75) Inventors: Chien-Hong Cheng, Hsinchu (TW); Kun-Yi Lu, Hsinchu (TW); Yu-Han Ou Yang, Hsinchu (TW); Cheng-Han Hsieh, Hsinchu (TW)

(73) Assignee: E INK HOLDINGS INC., Hsinchu (TW)

( * ) Notice: Subject to any disclaimer, the term of this patent is extended or adjusted under 35 U.S.C. 154(b) by 882 days.

(21) Appl. No.: 13/603,669

(22) Filed: Sep. 5, 2012

(65) Prior Publication Data

US 2013/0056716 A1 Mar. 7, 2013

Related U.S. Application Data

(60) Provisional application No. 61/531,321, filed on Sep. 6, 2011.

(51) Int. Cl.
| | |
|---|---|
| *H01L 51/54* | (2006.01) |
| *C09K 11/06* | (2006.01) |
| *C07F 15/00* | (2006.01) |
| *H01L 51/00* | (2006.01) |
| *H05B 33/10* | (2006.01) |
| *H01L 51/50* | (2006.01) |

(52) U.S. Cl.
CPC ........... *C09K 11/06* (2013.01); *C07F 15/0033* (2013.01); *H01L 51/0085* (2013.01); *H05B 33/10* (2013.01); *C09K 2211/1007* (2013.01); *C09K 2211/1011* (2013.01); *C09K 2211/1029* (2013.01); *C09K 2211/1044* (2013.01); *C09K 2211/185* (2013.01); *H01L 51/5016* (2013.01)

(58) Field of Classification Search
CPC .. C07F 15/0033; H01L 51/0085; H01L 51/50; H01L 51/5016; C09K 11/06; C09K 2211/1044; C09K 2211/1048; C09K 2211/1059; C09K 2211/1074; C09K 2211/185; H05B 33/10
See application file for complete search history.

(56) References Cited

U.S. PATENT DOCUMENTS

| | | | | |
|---|---|---|---|---|
| 7,960,547 | B2* | 6/2011 | Cheng et al. | 546/2 |
| 2004/0091738 | A1* | 5/2004 | Psai et al. | 428/690 |
| 2006/0228578 | A1* | 10/2006 | Ren et al. | C09K 11/06 |
| | | | | 428/690 |
| 2009/0149653 | A1* | 6/2009 | Cheng et al. | 546/4 |

FOREIGN PATENT DOCUMENTS

JP 2007/081014 A * 3/2007 ............. H01L 51/50

OTHER PUBLICATIONS

English language machine translation of JP 2007/081014 A, 2007.*

* cited by examiner

*Primary Examiner* — Marie R. Yamnitzky
(74) *Attorney, Agent, or Firm* — WPAT, PC; Justin King

(57) ABSTRACT

This invention provides transition metal carbene complexes and the electroluminescent application thereof. Through employing different N^N heteroleptic ligand, as the following, the transition metal carbene complex can display wide-range color tuning ability from deep blue to red. The mentioned transition metal carbene complex can be applied in luminescent device, and the luminescent device can display wide-range color tuning ability with high luminescent efficiency while employing different N^N heteroleptic ligand in the transition metal carbene complex.

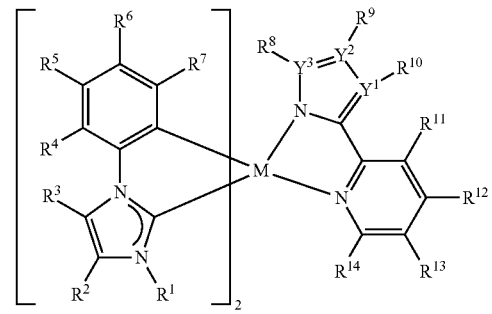

2 Claims, 7 Drawing Sheets

TRANSITION METAL CARBENE COMPLEXES AND THE ELECTROLUMINESCENT APPLICATION THEREOF

BACKGROUND OF THE INVENTION

1. Field of the Invention

The present invention is generally related to transition metal carbene complexes and the luminescent application thereof, and more particularly to transition metal biscarbene complexes and the electroluminescent application thereof.

2. Description of the Prior Art

In the previous reports, most researchers relied on the modification of C,N-heteroaromatic (C^N) ligand for wide-range altering of the emission wavelength and color. For example, fac-Ir(ppy)$_3$ (fac-tris(2-phenylpyridine)iridium) is well known to give green light emission. By increasing the conjugation of the ligand to 1-phenylisoquinoline in Ir(piq)$_3$ (tris[1-phenylisoquinolinato-C2,N]iridium), the emission of the iridium complex shifts from green to deep red. Other effective approaches for tuning the emission energy of cyclometalated iridium complexes include the introduction of electron withdrawing or donating groups to the aryl ring or pyridine rings and the use of different third ligand. The well-known light-blue iridium complex, FIrpic (iridium(III) bis(4,6-difluorophenylpyridinato-N,C$^{2'}$)picolinate) was designed based on the green emission Ir(ppy)$_2$(acac) (bis(2-phenylpyridine)(acetylacetonate)iridium(III)) by the introduction of electron-withdrawing fluoro groups to the phenyl ring and the use of pic ligand as the third ligand. A few other blue iridium complexes containing two 4,6-difluorophenylpyridinato-N,C$^{2'}$ ligands were also known to use various third ligands for the fine tune of the emission colors. Recently, Lee et al. synthesized a deeper blue dopant, FCNIr (tris((3,5-difluoro-4-cyanophenyl)pyridine)iridium) by the introduction of an electron withdrawing CN group to the 3,5-difluorophenyl)pyridine ligand. A device based on this complex as the dopant emitter showed high external quantum efficiency of 18.4% and CIE$_{x+y}$ (Commission Internationale de l'Eclairage)<0.30.

Iridium tris(carbene) complexes are known to have high triplet energy gaps and can be used as blue phosphorescent emitters. Kido et al. have reported a triscarbene iridium complex-based device having a high external quantum efficiency of 18.6% with CIE coordinate of (0.15, 0.19).

In the prior art, it is usually a hard trial to employ different corn structures and try to put different functional group thereon to form a new complex for providing different emitting color. Because it is a long and difficult process for synthesis a new proper luminescent material, it is a hard and expensive work to change the emitting color.

In view of the above matter, developing a novel transition metal carbene complex and device thereof having high luminance efficiency and wide-range color tuning is still an important task for the industry.

SUMMARY OF THE INVENTION

In light of the above background, in order to fulfill the requirements of the industry, the present invention provides a novel transition metal carbene complex and its application as emitting material in luminescent device.

One object of the present invention is to provide a transition metal carbene complexes and the luminescent application thereof, through changing the functional group on the transition metal carbene complexes, the luminescent performance of the transition metal carbene complexes can be efficiently improved.

Another object of the present invention is to provide transition metal carbene complexes and the luminescent application thereof, through employing the transition metal carbene complexes in the luminescent material of a luminescent device, the luminescent device displays wide-range color tuning ability with high phosphorescent efficiency.

Accordingly, the present invention discloses a transition metal carbene complexes and the luminescent application thereof. The general structure of the transition metal carbene complexes is as the following:

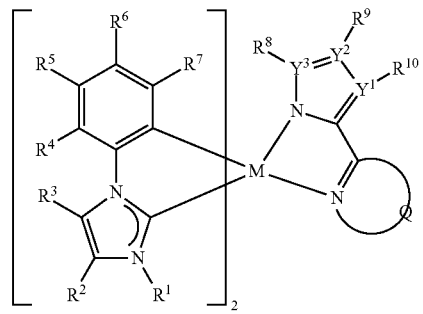

The mentioned transition metal carbene complex can provide great luminescent performance. Through modifying the ligand of the mentioned transition metal carbene complex, the transition metal carbene complex shows wide-range color tuning ability with high phosphorescent efficiency. Preferably, the transition metal carbene complex can be employed in the luminescent material of a luminescent device. More preferably, through modifying the ligand of the mentioned transition metal carbene complex, the luminescent device shows wide-range color tuning ability with high phosphorescent efficiency.

BRIEF DESCRIPTION OF THE DRAWINGS

The present disclosure can be described by the embodiments given below. It is understood, however, that the embodiments below are not necessarily limitations to the present disclosure, but are used to a typical implementation of the invention.

DESCRIPTION OF THE PREFERRED EMBODIMENTS

Figure 1:
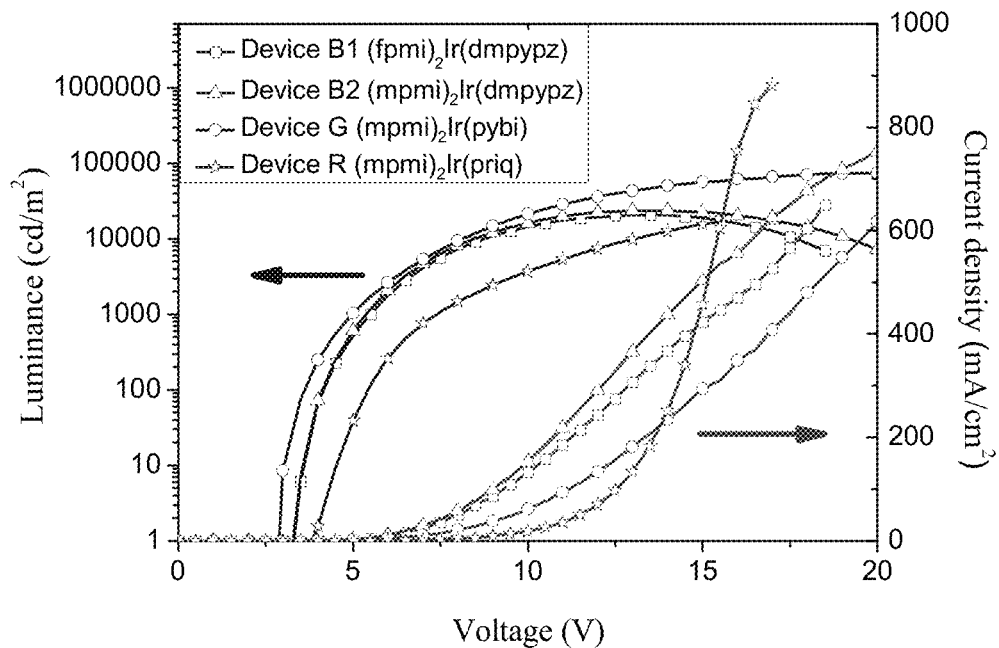
FIG. 1 shows the absorption and photoluminescence spectra of (fpmi)$_2$Ir(dmpypz), (mpmi)$_2$Ir(dmpypz), (mpmi)$_2$Ir(pybi), and (mpmi)$_2$Ir(priq) of this invention.
Figure 2:
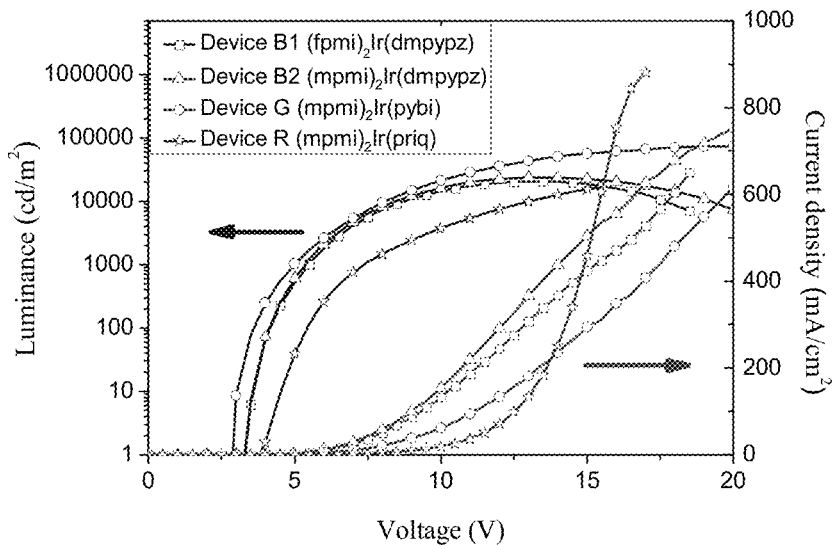
FIG. 2 shows the luminance and current density versus voltage for devices B1, B2, G, and R of this invention.
Figure 3:
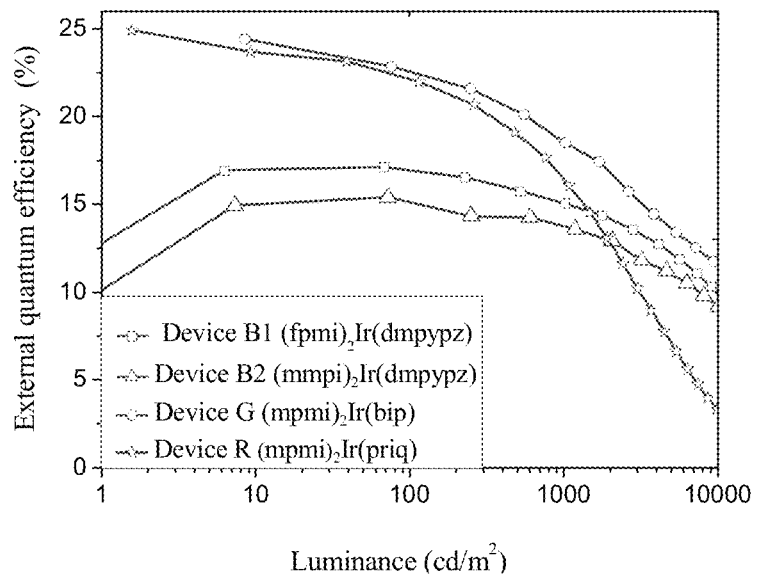
FIG. 3 shows the EQE versus luminance for devices B1, B2, G, and R of this invention.

What probed into the invention is transition metal carbene complex and the luminescent application thereof. Detailed descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater details in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

One preferred embodiment according to this specification discloses a transition metal carbene complex. The transition metal carbene complex is represented by the following formula:

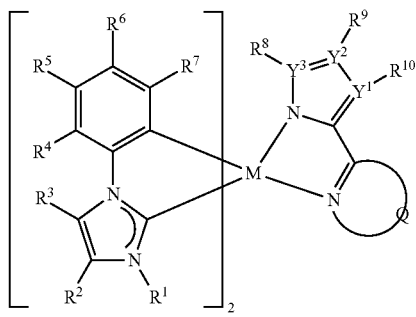

In the above formula, M is a transition metal and is selected from the group consisting of the following: ruthenium, rhodium, tungsten, rhenium, osmium, iridium, platinum, copper. $Y^1$, $Y^2$, and $Y^3$ can be identical or different, and are independently selected from the group consisting of the following: nitrogen (N), carbon (C), oxygen (O), sulfur (S). Q is a moiety comprising at least 3 atoms which contributes to a nitrogen-containing heterocycle, wherein Q comprises atom(s) selected from the group consisting of the following, or any combination thereof: nitrogen, carbon, oxygen, sulfur. The nitrogen-containing heterocycle optionally comprises one or more substituent. The substitutent(s) can be identical or different, and are independently selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, C1-C20 cycloalkyl group (for example methyl, ethyl, butyl, and cyclohexyl group), C1-C20 alkoxy group, C1-C20 substituted amino group, substituted arylamino group (for example aniline), nitrile group, nitro group, carbonyl group, cyano group (—CN), halogen substituted C1-C20 alkyl group (for example trifluoromethyl group, $CF_3$), and heterocyclic ring.

$R^1$ is selected from the group consisting of the following: C1-C20 alkyl group, C1-C20 cycloalkyl group, cycloalkenyl group, conjugated aromatic group, heterocyclic aromatic group. $R^2$~$R^{10}$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

In one preferred example of this embodiment, at least one of the following neighboring atom pairs $R^2$-$R^3$, $R^3$-$R^4$, $R^4$-$R^5$, $R^5$-$R^6$, $R^6$-$R^7$, $R^8$-$R^9$, $R^9$-$R^{10}$ forms an aromatic ring, heterocyclic aromatic group, cycloalkenyl group, or heterocyclic alkenyl group. The mentioned aromatic ring, heterocyclic aromatic group, cycloalkenyl group, or heterocyclic alkenyl group can be a five-membered, six-membered or seven-membered ring. Moreover, these aromatic ring, heterocyclic aromatic group, cycloalkenyl group, or heterocyclic alkenyl group can optionally comprise one or more substituent. The mentioned substituent is respectively selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

According to this example, the remaining ones of $R^2$~$R^{10}$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

The mentioned aryl group is selected from the group consisting of the following: phenyl, naphthyl, diphenyl, anthryl, pyrenyl, phenanthryl, and fluorenyl group. The above-mentioned heterocyclic aromatic group is selected from the group consisting of the following: pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline. The mentioned cycloalkenyl group is selected from the group consisting of the following: cyclohexene, cyclohexadiene, cyclopentene, cyclopentadiene. The nitrogen-containing heterocycle is selected from the group consisting of the following: pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline.

According to this embodiment, the transition metal carbene complex can be formed by a reaction with a halide-bridged dimer. The reaction is represented as the following:

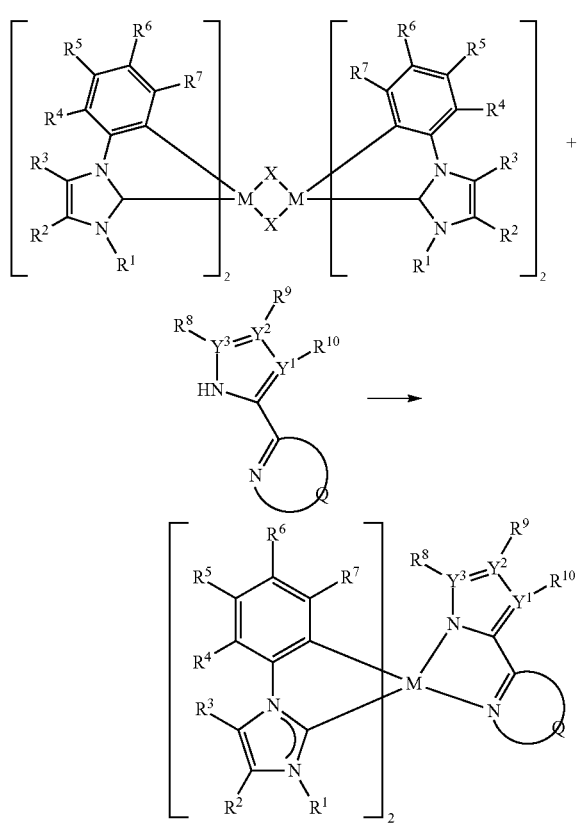

wherein X is halide atom, such as Cl, Br, I.

In one preferred example of this embodiment, the transition metal carbene complex is represented by the following formula:

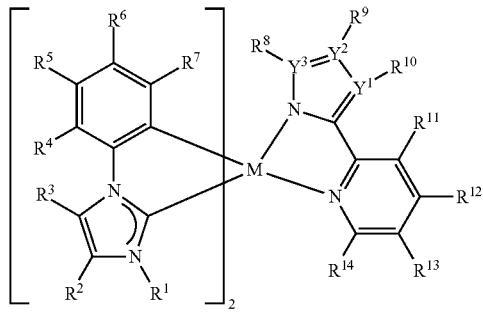

In the mentioned formula, $R^{11}$-$R^{14}$ can be identical or different, and can be independently selected from the group consisting of the following: H atom, halogen atom (such as F, Cl, Br, I), C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

In one preferred illustration of this example, the at least one of the following neighboring atom pairs $R^{10}$-$R^{11}$, $R^{11}$-$R^{12}$, $R^{12}$-$R^{13}$, forms an aromatic ring, heterocyclic aromatic group, cycloalkenyl group, or heterocyclic alkenyl group. The mentioned aromatic ring, heterocyclic aromatic group, cycloalkenyl group, or heterocyclic alkenyl group can be a five-membered, six-membered or seven-membered ring. Moreover, these aromatic ring, heterocyclic aromatic group, cycloalkenyl group, or heterocyclic alkenyl group can optionally comprise one or more substituent. The mentioned substituent is respectively selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

According to this illustration, the remaining ones of $R^{10}$~$R^{14}$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

In another preferred example of this embodiment, the transition metal carbene complex is represented by the following formula:

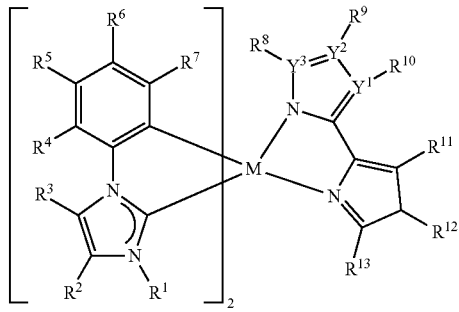

In the mentioned formula, $R^{11}$-$R^{13}$ can be identical or different, and are independently selected from the group consisting of the following: H atom, halogen atom (such as F, Cl, Br, I), C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

In one preferred illustration of this example, the at least one of the following neighboring atom pairs $R^{10}$-$R^{11}$, $R^{11}$-$R^{12}$, $R^{12}$-$R^{13}$ forms an aromatic ring, heterocyclic aromatic group, cycloalkenyl group, or heterocyclic alkenyl group. The mentioned aromatic ring, heterocyclic aromatic group, cycloalkenyl group, or heterocyclic alkenyl group can be a five-membered, six-membered or seven-membered ring. Moreover, these aromatic ring, heterocyclic aromatic group, cycloalkenyl group, or heterocyclic alkenyl group can optionally comprise one or more substituent. The mentioned substituent is respectively selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

According to this illustration, the remaining ones of $R^{10} \sim R^{13}$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

According to this embodiment, the above-mentioned transition metal carbene complex can be used in electroluminescent devices and/or phosphorescent devices, especially be used as the emitting material, electron transport material, or hole transport material in electroluminescent/phosphorescent devices. In addition, the disclosed transition metal complex can also be used as the electron transport material or hole transport material in other organic electronic devices, such as organic solar cells, organic thin-film transistors, organic photo-conductors or other organic semiconductor devices known to those skilled in the art.

Another preferred embodiment according to this specification discloses an electroluminescent device which comprises a pair of electrodes and at least one organic layer disposed between said electrodes. The above at least one organic layer comprises an emitting layer and a transition metal complex with carbene ligand, wherein the transition metal complex is represented by the following formula:

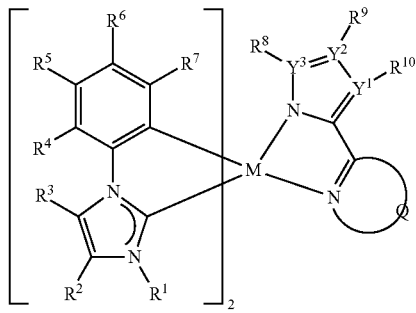

In the above formula, M is a transition metal and is selected from the group consisting of the following: ruthenium, rhodium, tungsten, rhenium, osmium, iridium, platinum, copper. $Y^1$, $Y^2$, and $Y^3$ can be identical or different, and are independently selected from the group consisting of the following: nitrogen (N), carbon (C), oxygen (O), sulfur (S). Q is a moiety comprising at least 3 atoms which contributes to a nitrogen-containing heterocycle, wherein Q comprises atom(s) selected from the group consisting of the following, or any combination thereof: nitrogen, carbon, oxygen, sulfur. The nitrogen-containing heterocycle optionally comprises one or more substituent. The substituent(s) can be identical or different, and are independently selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, electron donating group such as C1-C20 alkyl group and C1-C20 cycloalkyl group (for example methyl, ethyl, butyl, and cyclohexyl group), C1-C20 alkoxy group, C1-C20 substituted amino group, substituted arylamino group (for example aniline), or electron withdrawing group such as halogen atoms, nitrile group, nitro group, carbonyl group, cyano group (—CN), halogen substituted C1-C20 alkyl group (for example trifluoromethyl group, $CF_3$), and heterocyclic ring.

$R^1$ is selected from the group consisting of the following: C1-C20 alkyl group, C1-C20 cycloalkyl group, cycloalkenyl group, conjugated aromatic group, heterocyclic aromatic group; $R^2 \sim R^{10}$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

In one preferred example of this embodiment, at least one of the following neighboring atom pairs $R^2$-$R^3$, $R^3$-$R^4$, $R^4$-$R^5$, $R^5$-$R^6$, $R^6$-$R^7$, $R^8$-$R^9$, $R^9$-$R^{10}$ forms an aromatic ring, heterocyclic aromatic group, cycloalkenyl group, or heterocyclic alkenyl group. These mentioned aromatic ring, heterocyclic aromatic group, cycloalkenyl group, heterocyclic alkenyl group can be a five-membered, six-membered or seven-membered ring. Moreover, they optionally comprise one or more substituent. The mentioned substituent is respectively selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

According to this example, the remaining ones of $R^2 \sim R^{10}$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

The mentioned aryl group is selected from the group consisting of the following: phenyl, naphthyl, diphenyl, anthryl, pyrenyl, phenanthryl, and fluorenyl group. The above-mentioned heterocyclic aromatic group is selected from the group consisting of the following: pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline. The mentioned cycloalkenyl group is selected from the group consisting of the following: cyclohexene, cyclohexadiene, cyclopentene, cyclopentadiene. The nitrogen-containing heterocycle is selected from the group consisting of the following: pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline.

According to this embodiment, the transition metal carbene complex can be formed by a reaction with a halide-bridged dimer. The reaction is represented as the following:

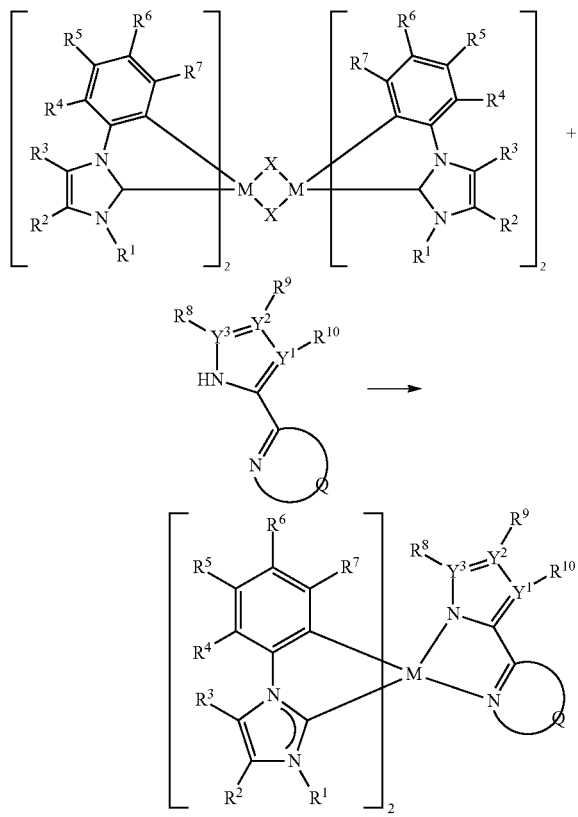

wherein X is halide atom, such as Cl, Br, I.

In one preferred example of this embodiment, the transition metal carbene complex is represented by the following formula:

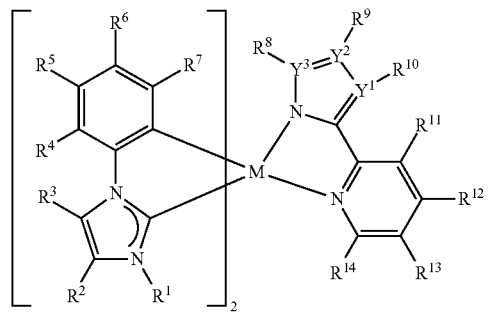

In the mentioned formula, $R^{11}$-$R^{14}$ can be identical or different, and can be independently selected from the group consisting of the following: H atom, halogen atom (such as F, Cl, Br, I), C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

In one preferred illustration of this example, the at least one of the following neighboring atom pairs $R^{10}$-$R^{11}$, $R^{11}$-$R^{12}$, $R^{12}$-$R^{13}$, forms an aromatic ring, heterocyclic aromatic group, cycloalkenyl group, or heterocyclic alkenyl group. The mentioned aromatic ring, heterocyclic aromatic group, cycloalkenyl group, or heterocyclic alkenyl group can be a five-membered, six-membered or seven-membered ring. Moreover, these aromatic ring, heterocyclic aromatic group, cycloalkenyl group, or heterocyclic alkenyl group can optionally comprise one or more substituent. The mentioned substituent is respectively selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

According to this illustration, the remaining ones of $R^{10}$~$R^{14}$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

In another preferred example of this embodiment, the transition metal carbene complex is represented by the following formula:

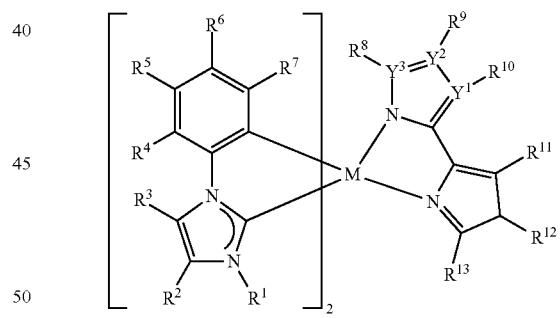

In the mentioned formula, $R^{11}$-$R^{13}$ can be identical or different, and are independently selected from the group consisting of the following: H atom, halogen atom (such as F, Cl, Br, I), C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

In one preferred illustration of this example, the at least one of the following neighboring atom pairs $R^{10}$-$R^{11}$, $R^{11}$-$R^{12}$, $R^{12}$-$R^{13}$ forms an aromatic ring, heterocyclic aromatic group, cycloalkenyl group, or heterocyclic alkenyl group. The mentioned aromatic ring, heterocyclic aromatic group, cycloalkenyl group, or heterocyclic alkenyl group can be a five-membered, six-membered or seven-membered ring. Moreover, these aromatic ring, heterocyclic aromatic group, cycloalkenyl group, or heterocyclic alkenyl group can optionally comprise one or more substituent. The mentioned substituent is respectively selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

According to this illustration, the remaining ones of $R^{10}$~$R^{13}$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

According to this embodiment, the above-mentioned transition metal carbene complex can be used in electroluminescent devices and/or phosphorescent devices, especially be used as the emitting material, electron transport material, or hole transport material in electroluminescent/phosphorescent devices. In addition, the disclosed transition metal complex can also be used as the electron transport material or hole transport material in other organic electronic devices, such as organic solar cells, organic thin-film transistors, organic photo-conductors or other organic semiconductor devices known to those skilled in the art.

According to this invention, in order to survey that the emission color of transition metal carbene complexes can be drastically tuned by using different heteroleptic N^N ligands, the following will disclose several examples and tests thereof with different transition metal carbene complexes. It is noted that these examples are not to limit the scope of the present invention, which should be determined in accordance with the claims.

For demonstrating, three heteroleptic iridium biscarbene complexes (mpmi)$_2$Ir(dmpypz), (mpmi)$_2$Ir(pybi), and (mpmi)$_2$Ir(priq) are synthesized, wherein H$_2$mpmiI=1-(4-tolyl)-3-methyl-imidazolium iodide, Hdmpypz 3,5-dimethyl-2-(1H-pyrazol-5-yl)pyridine, Hpybi=2-(pyridin-2-yl)-1H-benzo[d]imidazole and Hpriq=1-(1H-pyrrol-2-yl)isoquinoline. In these complexes, mpmi is the common carbene ligand and dmpypz, pybi and priq are the three N^N ligands. The reaction scheme for the synthesis of these complexes is shown in Scheme 1.

Scheme 1. The structures of (fpmi)$_2$Ir(dmpypz), (mpmi)$_2$Ir(dmpypz), (mpmi)$_2$Ir(pybi), and (mpmi)$_2$Ir(priq)

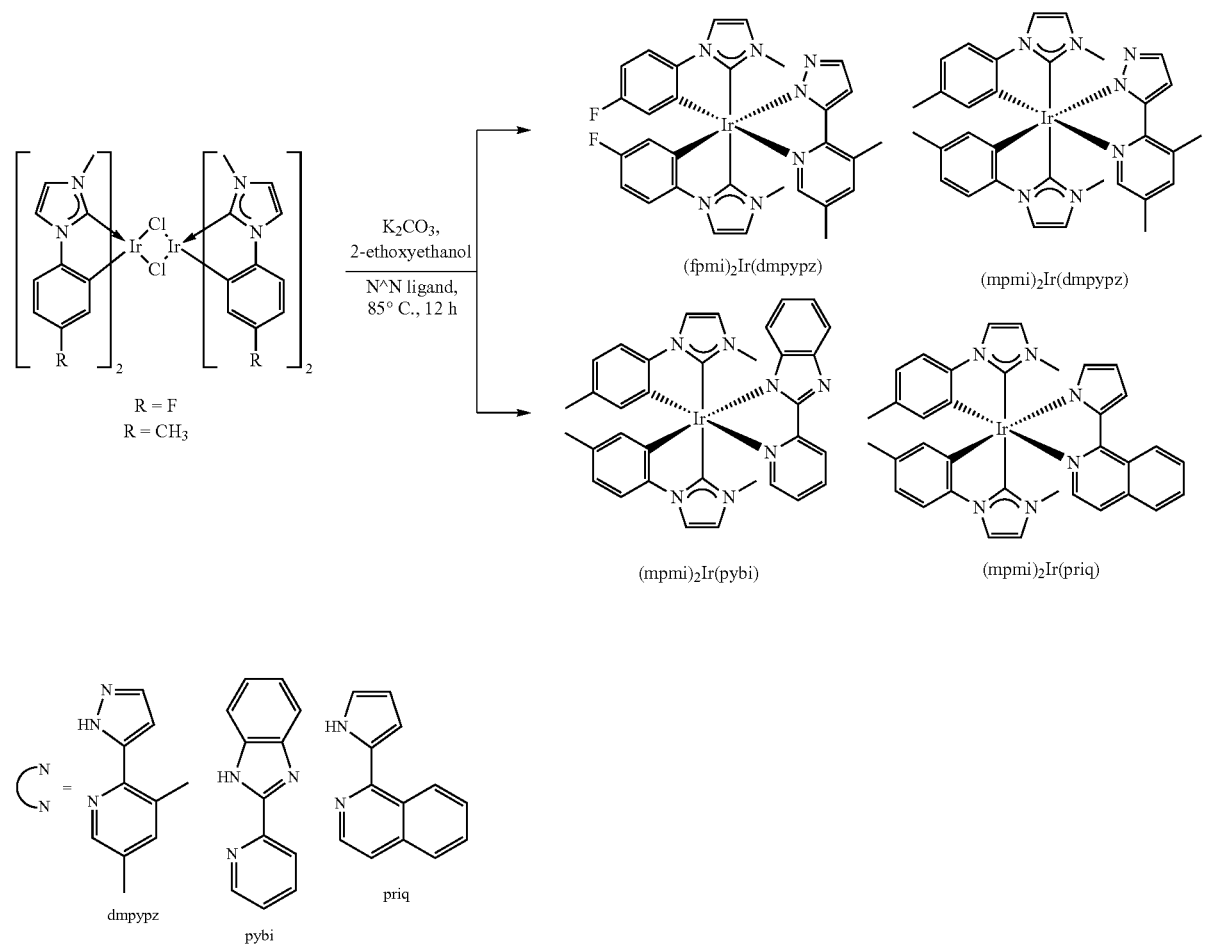

Figure 4:
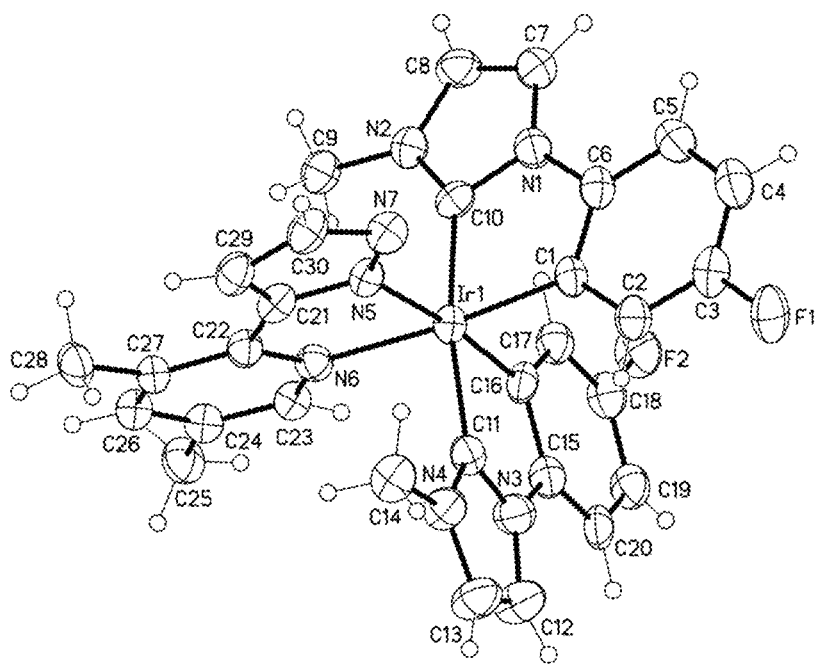
FIG. 4 shows the ORTEP diagram of complex (fpmi)$_2$Ir(dmpypz)
Figure 5:
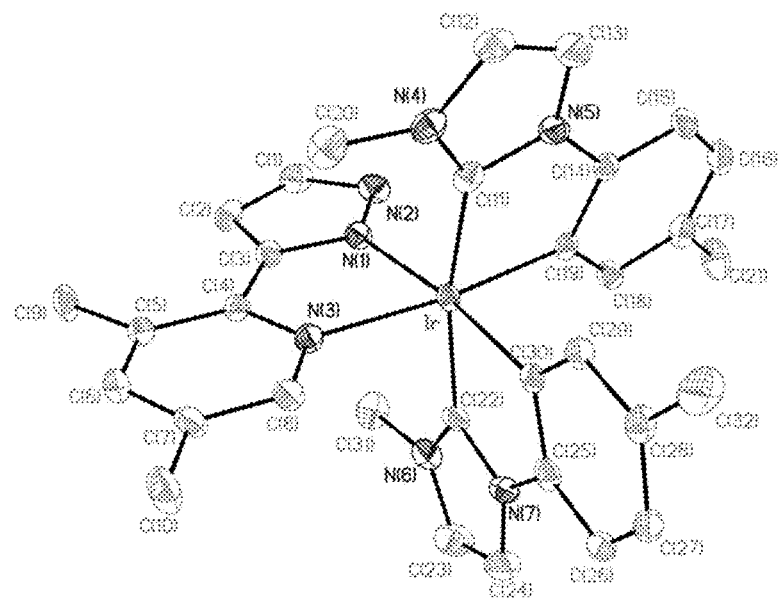
FIG. 5 shows the ORTEP diagram of complex (mpmi)$_2$Ir(dmpypz)
Figure 6:
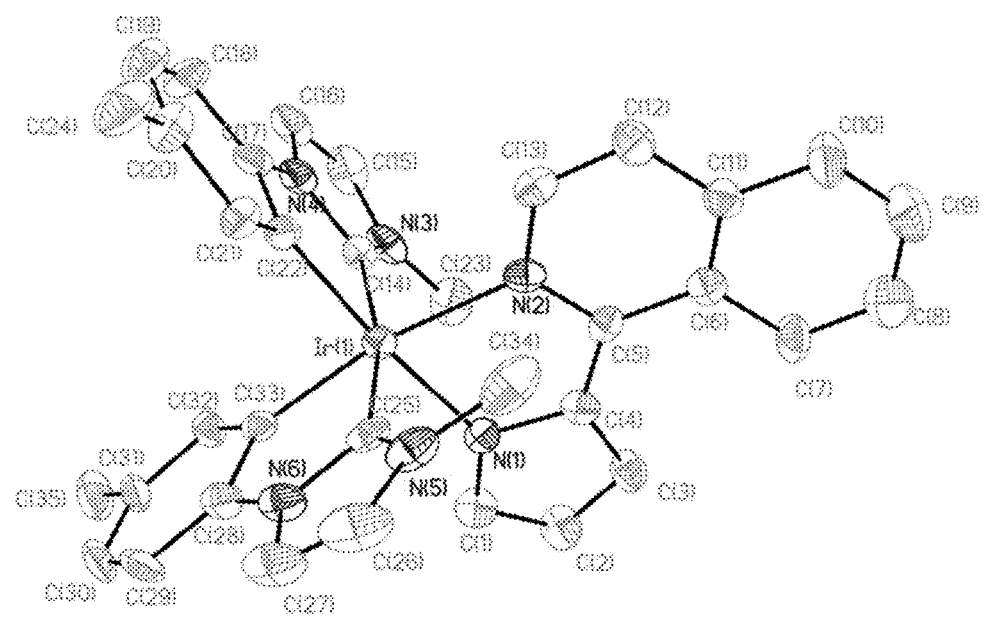
FIG. 6 shows the ORTEP diagram of complex (mpmi)$_2$Ir(priq)

First, iridium trichloride hydrate in 2-ethoxyethanol was treated with silver oxide and the carbene precursor H₂mpmiI to give the chloride-bridged dimer. Further reaction of the dimer with the N^N ligands Hdmpypz, Hpybi, and Hpriq afforded complexes (mpmi)₂Ir(dmpypz), (mpmi)₂Ir(pybi), and (mpmi)₂Ir(priq), respectively, in excellent yields. To further tune the emission of these iridium complexes to deeper blue, we also prepared (fpmi)₂Ir(dmpypz) employing carbene precursor 1-(4-fluorophenyl)-3-methyl-imidazolium iodide (H₂fpmiI) for the synthesis of the corresponding iridium dimer. Further treatment of the dimer with Hdmpypz gave the expected iridium dicarbene complex. The structures of these complexes were determined by single-crystal X-ray diffraction. The results revealed that all these heteroleptic iridium complexes are distorted octahedral with the two carbene groups being trans to each other and the two 4-tolyl (4-fluoro phenyl for (fpmi)₂Ir(dmpypz)) groups occupying the cis positions (see FIG. 4-FIG. 6). The $^1$H and $^{13}$C NMR spectra, mass data and elemental analysis of these products further confirmed the proposed structures.

Several transition metal complexes will be given below as examples constructed according to the presented invention. It is noted that these examples are not to limit the scope of the present invention, which should be determined in accordance with the claims.

EXPERIMENTAL

Example 1

Preparation of (fpmi)₂Ir(dmpypz)

[Iridium(III) bis(1-(4-fluorophenyl)-3-methylimidazolin-2-ylidene-C,C2')(3,5-dimethyl-2-(1H-pyrazol-5-yl)pyridinato)]

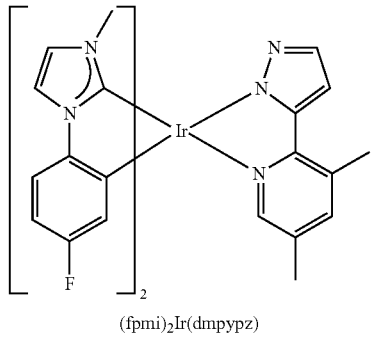

(fpmi)₂Ir(dmpypz)

Procedure for the Synthesis of (fpmi)₂Ir(dmpypz):

A mixture of [(fpmi)₂IrCl]₂ (0.250 mmol, 289 mg), 3,5-dimethyl-2-(1H-pyrazol-5-yl)pyridine (0.55 mmol, 95 mg) and K₂CO₃ (0.55 mmol, 76 mg) in 2-ethoxyethanol (1.0 mL) was heated at 85° C. under nitrogen atmosphere for 12 h. The reaction mixture was cooled to ambient temperature and filtered. The residue was washed with methanol to give the desired bright-yellow powder (354 mg) in 99% yield. $^1$H NMR (400 MHz, CDCl₃, δ): 7.66 (s, 2H), 7.32-7.28 (m, 3H), 7.01-6.95 (m, 2H), 6.76 (d, J=2 Hz, 1H), 6.70-6.69 (m, 2H), 6.58-6.49 (m, 2H), 6.13 (dd, J=1.2 Hz, J=9.6 Hz, 1H), 6.05 (dd, J=2.8 Hz, J=10 Hz, 1H), 2.94 (s, 3H), 2.92 (s, 3H), 2.57 (s, 3H), 2.07 (s, 3H); $^{13}$C NMR (150 MHz, CDCl₃, δ): 171.7 (C4), 171.3 (C4), 160.7 (C4, $J_{C-F}$=243 Hz), 160.2 (C4, $J_{C-F}$=242.1 Hz), 152.9 (C4), 148.4 (C4), 148.3 (C3), 143.6 (C4), 143.0 (C4), 142.9 (C4), 139.8 (C3), 139.5 (C3), 136.7 (C4), 130.4 (C4), 129.3 (C4), 123.8 (C3, $J_{C-F}$=17.7 Hz), 123.6 (C3, $J_{C-F}$=18.6 Hz), 121.5 (C3), 121.0 (C3), 114.8 (C3), 114.6 (C3), 111.4 (C3, $J_{C-F}$=8.85 Hz), 111.1 (C3, $J_{C-F}$=9.15 Hz), 107.2 (C3, $J_{C-F}$=24.75 Hz), 107.0 (C3, $J_{C-F}$=24.75 Hz), 106.3 (C3), 34.9 (C1), 34.7 (C1), 21.1 (C1), 17.8 (C1); HRMS (FAB⁺) calcd for C₃₀H₂₆F₂IrN₇, 715.1847. Found, 715.1848; Anal. calcd for C, 50.41; H, 3.67; N, 13.72. Found, C, 50.36; H, 3.78; N, 13.59.

Procedures similar to that for (fpmi)₂Ir(dmpypz) were used to prepare several transition metal carbene complexes with corresponding halide-bridged dimer and ligand. The data of those complexes is as following.

Example 2

(mpmi)₂Ir(dmpypz)

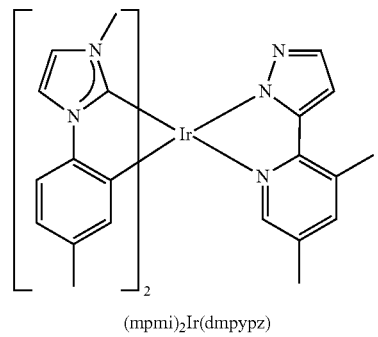

(mpmi)₂Ir(dmpypz)

[Iridium(III) bis(1-(4-methylphenyl)-3-methylimidazolin-2-ylidene-C,C2')(3,5-dimethyl-2-(1H-pyrazol-5-yl)pyridinato)]

bright-yellow powder (350 mg, 99%). $^1$H NMR (400 MHz, CD₂Cl₂, δ): 7.75 (s, 1H), 7.57 (d, J=2 Hz, 1H), 7.42 (d, J=2 Hz, 1H), 7.39 (d, J=2 Hz, 1H), 7.32 (s, 1H), 7.02-6.98 (m, 2H), 6.81 (t, J=2 Hz, 2H), 6.71-6.66 (m, 3H), 6.30 (d, J=1.6 Hz, 1H), 6.19 (d, J=1.6 Hz, 1H), 2.96 (s, 3H), 2.93 (s, 3H), 2.59 (s, 3H), 2.14 (s, 3H), 2.12 (s, 3H), 2.07 (s, 3H); $^{13}$C NMR (150 MHz, CD₂Cl₂, δ): 172.4 (C4), 150.0 (C4), 149.6 (C3), 145.8 (C4), 140.7 (C3), 139.6 (C3), 139.4 (C3), 137.2 (C4), 135.6 (C4), 135.0 (C4), 122.7 (C3), 122.3 (C3), 122.1 (C3), 121.8 (C3), 115.4 (C3), 115.2 (C3), 111.6 (C3), 111.4 (C3), 107.3 (C3), 35.7 (C1), 35.5 (C1), 21.9 (C1), 21.6 (C1), 18.4 (C1); HRMS (FAB⁺) calcd for C₃₂H₃₂IrN₇, 707.2348. Found, 707.2354. Anal. calcd for C, 54.37; H, 4.56; N, 13.87. Found, C, 54.31; H, 4.35; N, 14.05.

Example 3

(fpmi)₂Ir(mpypz)

[Iridium(III) bis(1-(4-fluorophenyl)-3-methylimidazolin-2-ylidene-C,C2')(4-methyl-2-(1H-pyrazol-5-yl)pyridinato)]

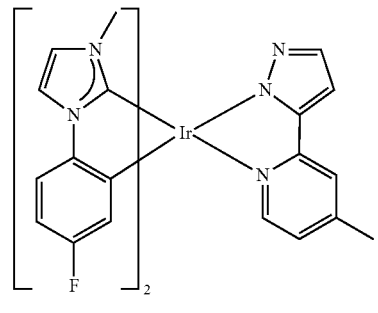

(fpmi)₂Ir(mpypz)

¹H NMR (400 MHz, CDCl₃, δ): 7.68 (d, J=5.6 Hz, 1H), 7.58 (d, J=2 Hz, 1H), 7.44 (t, J=0.8 Hz, 1H), 7.30-7.28 (m, 2H), 7.00-6.94 (m, 2H), 6.76 (d, J=2 Hz, 1H), 6.70 (t, J=2 Hz, 1H), 6.65 (d, J=2 Hz, 1H), 6.60-6.48 (m, 3H), 6.15 (dd, J=2.8 Hz, J=9.2 Hz, 1H), 6.08 (dd, J=2.4 Hz, J=9.6 Hz, 1H), 2.99 (s, 3H), 2.98 (s, 3H), 2.36 (s, 3H); HRMS (FAB⁺) calcd for $C_{29}H_{24}F_2IrN_7$, 701.1690. Found, 701.1694; Anal. calcd for C, 49.70; H, 3.45; N, 13.99. Found, C, 49.61; H, 3.79; N, 13.7.

Example 4

(fpmi)₂Ir(tBupypz)

[Iridium(III) bis(1-(4-fluorophenyl)-3-methylimidazolin-2-ylidene-C,C²')(4-tert-butyl-2-(1H-pyrazol-5-yl)pyridinato)]

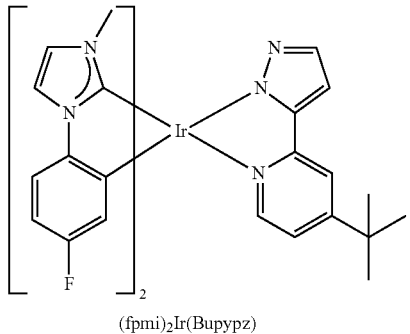

(fpmi)₂Ir(Bupypz)

¹H NMR (400 MHz, CDCl₃, δ): 7.73 (dd, J=0.8 Hz, J=6 Hz, 1H), 7.59 (d, J=2 Hz, 1H), 7.57 (dd, J=0.8 Hz, J=2.4 Hz, 1H), 7.31-7.30 (m, 2H), 6.98 (td, J=4.8 Hz, J=8.8 Hz, 2H), 6.80 (dd, J=2.4 Hz, J=6 Hz, 1H), 6.78 (d, J=2 Hz, 1H), 6.71 (d, J=2 Hz, 1H), 6.67 (d, J=2 Hz, 1H), 6.57-6.49 (m, 2H), 6.16 (dd, J=2.8 Hz, J=9.2 Hz, 1H), 6.08 (dd, J=2.8 Hz, J=9.6 Hz, 1H), 3.01 (s, 3H), 2.96 (s, 3H), 1.29 (s, 9H); HRMS (FAB⁺) calcd for $C_{32}H_{30}F_2IrN_7$, 743.2160. Found, 743.2156; Anal. calcd for C, 51.74; H, 4.07; N, 13.20. Found, C, 51.60; H, 4.31; N, 13.03.

Example 5

(dfpmi)₂Ir(mpypz)

[Iridium(III) bis(1-(2,4-difluorophenyl)-3-methyl-imidazolin-2-ylidene-C,C²')(4-methyl-2-(1H-pyrazol-5-yl)pyridinato)]

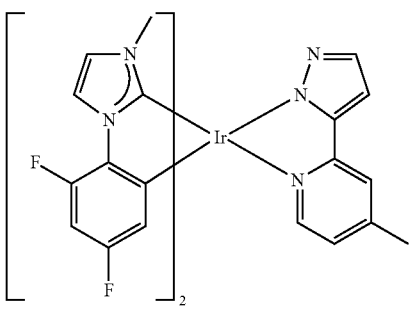

(dfpmi)₂Ir(mpypz)

¹H NMR (400 MHz, CDCl₃, δ): 7.70 (dd, J=1.2 Hz, J=2.0 Hz, 1H), 7.68 (t, J=2 Hz, 1H), 7.63 (d, J=5.6 Hz, 1H), 7.59 (d, J=2 Hz, 1H), 7.45 (d, J=0.8 Hz, 1H), 6.76 (d, J=2 Hz, 1H), 6.72 (d, J=2 Hz, 1H), 6.66 (d, J=2 Hz, 1H), 6.63 (dd, J=1.6 Hz, J=6 Hz, 1H), 6.45-6.33 (m, 2H), 5.93 (dd, J=2.4 Hz, J=8.8 Hz, 1H), 5.85 (dd, J=2 Hz, J=8.8 Hz, 1H), 3.00 (s, 3H), 2.99 (s, 3H), 2.38 (s, 3H); HRMS (FAB⁺) calcd for $C_{29}H_{22}F_4IrN_7$, 737.1502. Found, 737.1497.

Example 6

(dfpmi)₂Ir(tBupypz)

[Iridium(III) bis(1-(2,4-difluorophenyl)-3-methyl-imidazolin-2-ylidene-C,C²)(4-tert-butyl-2-(1H-pyrazol-5-yl)pyridinato]

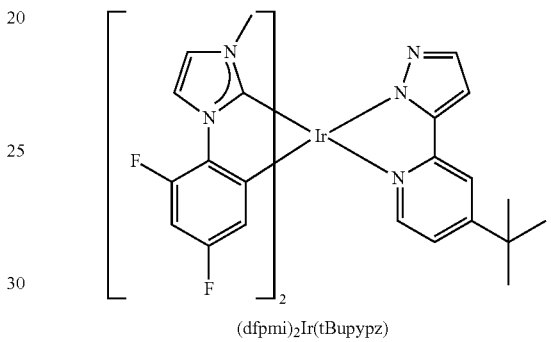

(dfpmi)₂Ir(tBupypz)

¹H NMR (400 MHz, CDCl₃, δ): 7.71-7.68 (m, 4H), 7.62 (d, J=1.6 Hz, 1H), 6.89 (d, J=4.4 Hz, 1H), 6.79 (d, J=2 Hz, 1H), 6.79-6.69 (m, 2H), 6.43-6.39 (m, 2H), 5.92 (dd, J=2.4 Hz, J=8.8 Hz, 1H), 5.84 (dd, J=2.4 Hz, J=8.8 Hz, 1H), 3.02 (s, 3H), 2.96 (s, 3H), 1.31 (s, 9H); HRMS (FAB⁺) calcd for $C_{32}H_{28}F_4IrN_7$, 779.1972. Found, 779.1968.

Example 7

(dfpmi)₂Ir(dmpypz)

[Iridium(III) bis(1-(2,4-difluorophenyl)-3-methyl-imidazolin-2-ylidene-C,C²') (3,5-dimethyl-2-(1H-pyrazol-5-yl)pyridinato)]

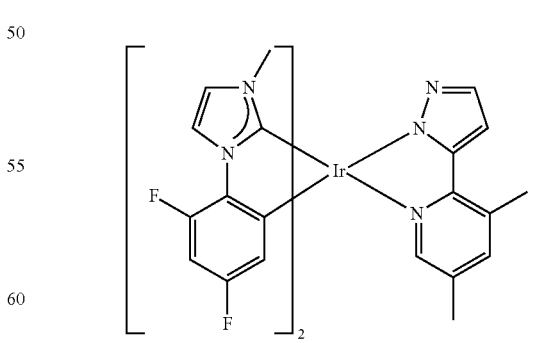

(dfpmi)₂Ir(dmpypz)

¹H NMR (400 MHz, CDCl₃, δ): 7.70 (d, J=1.2 Hz, 2H), 7.65 (d, J=2 Hz, 1H), 7.60 (s, 1H), 7.29 (s, 1H), 6.75 (d, J=1.2 Hz, 1H), 6.70 (dd, J=1.6 Hz, J=4 Hz, 2H), 6.45-6.33

(m, 2H), 5.92 (dd, J=2.4 Hz, J=8.8 Hz, 1H), 5.82 (dd, J=2.4 Hz, J=8.8 Hz, 1H), 2.92 (s, 6H), 2.57 (s, 3H), 2.09 (s, 3H); HRMS (FAB$^+$) calcd for $C_{30}H_{24}F_4IrN_7$, 751.1659. Found, 751.1652; Anal. calcd for C, 47.99; H, 3.22; N, 13.06. Found, C, 47.96; H, 2.88; N, 12.99.

Example 8

(mpmi)$_2$Ir(pypr)

[Iridium(III) bis(1-(4-methylphenyl)-3-methylimidazolin-2-ylidene-C,C$^{2'}$)(2-(1H-pyrrol-2-yl)pyridinato)]

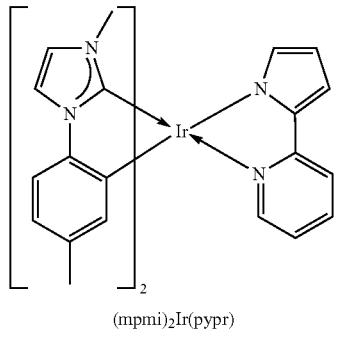

(mpmi)$_2$Ir(pypr)

$^1$H NMR (400 MHz, CDCl$_3$, δ): 7.69-7.67 (m, 1H), 7.44-7.41 (m, 1H), 7.35 (dd, J=1.6 Hz, J=5.6, 1 Hz), 7.31 (dd, J=2.0 Hz, J=6.4 Hz, 2H), 6.93 (d, J=12 Hz, 1H), 6.91 (d, J=12 Hz, 1H), 6.75 (dd, J=1.6 Hz, J=3.6 Hz, 1H), 6.71 (dd, J=2.0 Hz, J=10.4 Hz, 2H), 6.64-6.59 (m, 2H), 6.46-6.42 (m, 1H), 6.38 (d, J=2 Hz, 1H), 6.30 (d, J=1.2 Hz, 1H), 6.25 (t, J=1.6 Hz, 1H), 6.12 (dd, J=1.6 Hz, J=3.6 Hz, 1H), 3.10 (s, 3H), 2.98 (s, 3H), 2.12 (s, 3H), 2.10 (s, 3H); HRMS (FAB$^+$) calcd for $C_{31}H_{29}IrN_6$, 678.2083. Found, 678.2089; Anal. calcd for C, 54.93; H, 4.31; N, 12.40. Found, C, 54.99; H, 4.27; N, 12.43.

Example 9

(mpmi)$_2$Ir(dmpypr)

[Iridium(III) bis(1-(4-methylphenyl)-3-methylimidazolin-2-ylidene-C,C$^{2'}$)(3,5-dimethyl-2-(1H-pyrrol-2-yl)pyridinato)]

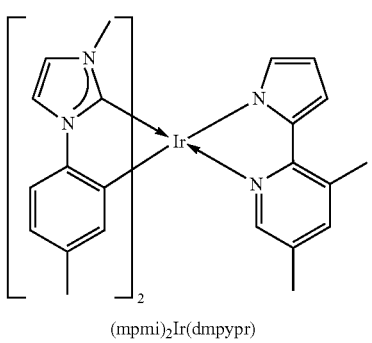

(mpmi)$_2$Ir(dmpypr)

$^1$H NMR (400 MHz, CDCl$_3$, δ): 7.56 (s, 1H), 7.31 (d, J=2 Hz, 1H), 7.28 (d, J=2 Hz, 1H), 7.08 (s, 1H), 6.92 (d, J=10.8 Hz, 1H), 6.90 (d, J=10.8 Hz, 1H), 6.76 (dd, J=1.2 Hz, J=4 Hz, 1H), 6.69 (dd, J=1.6 Hz, J=10 Hz, 2H), 6.60 (t, J=8 Hz, 2H), 6.35 (s, 1H), 6.30 (d, J=1.6 Hz, 1H), 6.28 (s, 1H), 6.17 (dd, J=1.6 Hz, J=3.6 Hz, 1H), 3.02 (s, 3H), 2.90 (s, 3H), 2.50 (s, 3H), 2.12 (s, 3H), 2.10 (s, 3H), 1.97 (s, 3H); HRMS (FAB$^+$) calcd for $C_{33}H_{33}IrN_6$, 706.2396. Found, 706.2394; Anal. calcd for C, 56.15; H, 4.71; N, 11.91. Found, C, 56.16; H, 4.50; N, 11.97.

Example 10

(mpmi)$_2$Ir(pybi)

[Iridium(III) bis(1-(4-methylphenyl)-3-methylimidazolin-2-ylidene-C,C$^{2'}$)(2-(pyridin-2-yl)-1H-benzo[d]imidazole)]

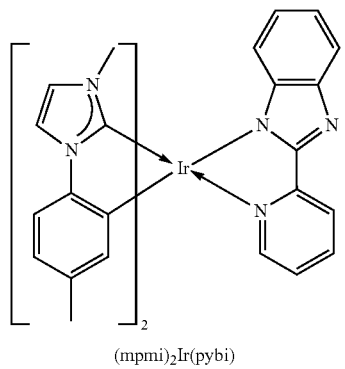

(mpmi)$_2$Ir(pybi)

yellow powder (357 mg, 98%). $^1$H NMR (400 MHz, CDCl$_3$, δ): 8.41 (dd, J=0.8 Hz, J=8 Hz, 1H), 7.97-7.95 (m, 1H), 7.70 (td, J=1.6 Hz, J=8 Hz, 1H), 7.66 (dd, J=0.8 Hz, J=8 Hz, 1H), 7.35 (d, J=1.6 Hz, 1H), 7.27 (d, J=2 Hz, 1H), 7.01-6.94 (m, 4H), 6.73-6.65 (m, 5H), 6.35 (dd, J=1.2 Hz, J=13.6 Hz, 2H), 6.12 (dd, J=0.8 Hz, J=8 Hz, 1H), 2.95 (s, 3H), 2.82 (s, 3H), 2.14 (s, 6H); $^{13}$C NMR (150 MHz, CDCl$_3$, δ): 172.8 (C4), 172.6 (C4), 160.0 (C4), 155.3 (C4), 150.6 (C3), 146.7 (C4), 145.6 (C4), 145.2 (C4), 145.2 (C4), 139.4 (C3), 139.1 (C3), 138.5 (C4), 136.2 (C3), 134.6 (C4), 133.8 (C4), 132.0 (C4), 123.3 (C3), 121.9 (C3), 121.7 (C3), 121.6 (C3), 121.1 (C3), 120.9 (C3), 120.6 (C3), 120.2 (C3), 118.6 (C3), 116.2 (C3), 114.4 (C3), 114.3 (C3), 110.6 (C3), 110.3 (C3), 35.0 (C1), 34.9 (C1), 21.5 (C1), 21.4 (C1); HRMS (FAB$^+$) calcd for $C_{34}H_{30}IrN_7$, 729.2192. Found, 729.2188; Anal. calcd for C, 56.03; H, 4.15; N, 13.45. Found, C, 55.77; H, 3.90; N, 13.45.

Example 11

(mpmi)$_2$Ir(biiq)

[Iridium(III) bis(1-(4-methylphenyl)-3-methylimidazolin-2-ylidene-C,C$^{2'}$)(1-(1H-benzo[d]imidazol-2-yl)isoquinolinato)]

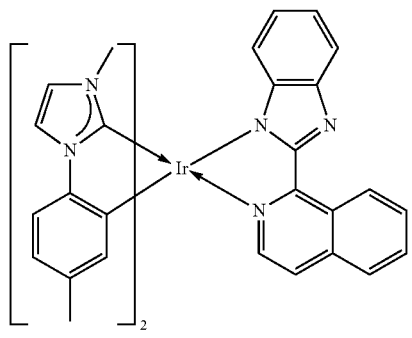

(mpmi)$_2$Ir(biiq)

¹H NMR (400 MHz, CDCl₃, δ): 8.03 (d, J=6.4 Hz, 1H), 7.84-7.76 (m, 4H), 7.67 (d, J=8 Hz, 1H), 7.40 (dd, J=2 Hz, J=7.6 Hz, 2H), 7.30 (d, J=6.4 Hz, 1H), 7.07 (dd, J=1.6 Hz, J=7.6 Hz, 2H), 7.00 (td, J=1.2 Hz, J=7.4 Hz, 1H), 6.81-6.80 (m, 5H), 6.41 (d, J=1.2 Hz, 1H), 6.36 (s, 1H), 6.27 (d, J=8 Hz, 1H), 2.91 (s, 3H), 2.76 (s, 3H), 2.19 (s, 3H), 2.18 (s, 3H); HRMS (FAB⁺) calcd for $C_{38}H_{32}IrN_7$, 779.2348. Found, 779.2341; Anal. calcd for C, 58.59; H, 4.14; N, 12.59. Found, C, 58.27; H, 4.06; N, 12.73.

Example 12

(mpmi)₂Ir(priq)

[Iridium(III) bis(1-(4-methylphenyl)-3-methylimidazolin-2-ylidene-C,C²')(1-(1H-pyrrol-2-yl)isoquinolinato)]

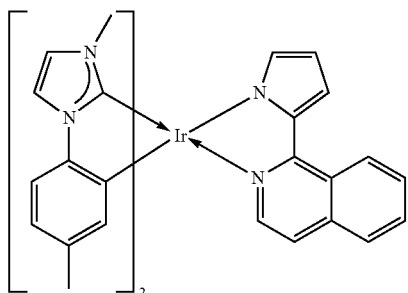

(mpmi)₂Ir(priq)

¹H NMR (400 MHz, CDCl₃, δ): 8.94-8.92 (m, 1H), 7.71 (d, J=6.4 Hz, 1H), 7.61-7.53 (m, 3H), 7.32-7.30 (m, 3H), 6.95 (d, J=13.6 Hz, 1H), 6.93 (d, J=13.2 Hz, 1H), 6.79 (d, J=6 Hz, 1H), 6.68-6.61 (m, 4H), 6.42-6.41 (m, 1H), 6.39 (d, J=1.2 Hz, 1H), 6.32 (d, J=1.2 Hz, 1H), 6.29 (dd, J=1.6 Hz, J=3.6 Hz, 1H), 3.03 (s, 3H), 2.93 (s, 3H), 2.14 (s, 3H), 2.11 (s, 3H); ¹³C NMR (150 MHz, CDCl₃, δ): 173.6 (C4), 172.8 (C4), 157.7 (C4), 145.4 (C4), 145.0 (C4), 143.9 (C3), 141.8 (C4), 139.4 (C3), 139.1 (C3), 138.9 (C4), 136.5 (C4), 135.9 (C4), 134.5 (C3), 134.2 (C4), 135.5 (C4), 129.7 (C3), 126.9 (C3), 126.8 (C3), 126.7 (C3), 124.4 (C4), 121.0 (C3), 120.8 (C3), 120.8 (C3), 120.5 (C3), 115.5 (C3), 115.4 (C3), 114.1 (C3), 114.1 (C3), 110.6 (C3), 110.2 (C3), 109.9 (C3), 35.2 (C1), 34.2 (C1), 21.5 (C1), 21.4 (C1); HRMS (FAB⁺) calcd for $C_{35}H_{31}IrN_6$, 728.2239. Found, 728.2234; Anal. calcd for C, 57.75; H, 4.29; N, 11.55. Found, C, 57.77; H, 3.93; N, 11.61.

Example 13

(mpmi)₂Ir(bipa)

[Iridium(III) bis(1-(4-methylphenyl)-3-methylimidazolin-2-ylidene-C,C²')(2-(pyrazin-2-yl)-1H-benzo[d]imidazole)]

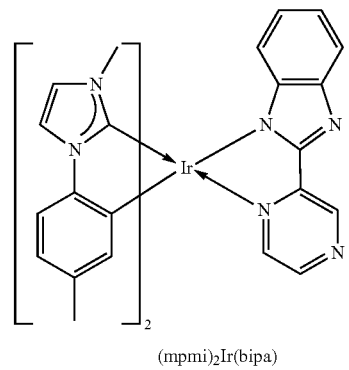

(mpmi)₂Ir(bipa)

¹H NMR (400 MHz, CDCl₃, δ): 9.63 (s, 1H), 8.16 (d, J=3.2 Hz, 1H), 7.94 (d, J=2 Hz, 1H), 7.70 (d, J=8.4 Hz, 1H), 7.37 (d, J=1.6 Hz, 1H), 7.29 (d, J=1.6 Hz, 1H), 7.05 (t, J=7.6 Hz, 1H), 7.01-6.98 (m, 2H), 6.78-6.68 (m, 5H), 6.36 (s, 1H), 6.29 (s. 1H), 6.14 (d, J=8.4 Hz, 1H), 2.99 (s, 3H), 2.80 (s, 3H), 2.14 (s, 3H), 2.14 (s, 3H); HRMS (FAB⁺) calcd for $C_{33}H_{29}IrN_8$, 730.2144. Found, 730.2144; Anal. calcd for C, 54.31; H, 4.00; N, 15.35. Found, C, 54.31; H, 3.72; N, 15.40.

Example 14

(mpmi)₂Ir(biq)

[Iridium(III) bis(1-(4-methylphenyl)-3-methylimidazolin-2-ylidene-C,C²')(2-(1H-benzo[d]imidazol-2-yl)quinolinato)]

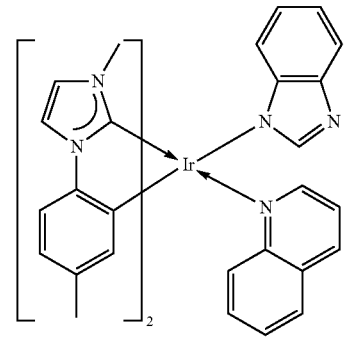

(mpmi)₂Ir(biq)

¹H NMR (400 MHz, CDCl₃, δ): 8.71 (d, J=8.4 Hz, 1H), 8.20 (d, J=8.8 Hz, 1H), 8.12 (d, J=8.8 Hz, 1H), 7.69 (t, J=8 Hz, 2H), 7.34-7.30 (m, 3H), 7.09 (t, J=7.2 Hz, 1H), 7.01 (t, J=7.2 Hz, 1H), 6.95 (t, J=8 Hz, 2H), 6.74-6.67 (m, 4H), 6.62 (d, J=2 Hz, 1H), 6.36 (s, 1H), 6.10 (s, 1H), 5.91 (d, J=8.8 Hz, 1H), 2.84 (s, 3H), 2.69 (s, 3H), 2.14 (s, 3H), 2.10 (s, 3H); HRMS (FAB⁺) calcd for $C_{38}H_{32}IrN_7$, 779.2348. Found, 779.2343.

The UV-visible absorption and photoluminescence (PL) spectra of these iridium biscarbene complexes are depicted in FIG. 1 and the absorption and emission maxima are summarized in Table 1.

TABLE 1

The photophysical and electrochemical properties of iridium biscarbene complexes.

| Heteroleptic Complex | Absorption λ (nm) (ε,10³M⁻¹ cm⁻¹)[a] | PL (nm) RT[a] | PL (nm) 77K[b] | Rigido-chromic Shift (nm)[c] | HOMO[d]/ LUMO[e]/ $E_s$(eV)[f] | τ (μs) [a][g] | $\Phi_{PL}$ (%)[h] |
|---|---|---|---|---|---|---|---|
| (fpmi)₂Ir(dmpypz) | 275(58), 301(42), 364(8) | 455 | 442 | 13 | 5.2/2.0/ 3.2 | 0.07, 1.84 | 58.7 |
| (mpmi)₂Ir(dmpypz) | 276(84), 320(17), 363(4) | 466 | 443 | 23 | 5.1/1.9/ 3.2 | 0.38, 2.24 | 41.6 |
| (mpmi)₂Ir(pybi) | 301(39), 340(43), 358(39), 401(7) | 530 | 507 | 23 | 5.1/2.3/ 2.8 | 1.32 | 79.3 |
| (mpmi)₂Ir(priq) | 272(59), 324(44), 420(38), 488(1.2) | 599 | 579 | 20 | 5.0/2.3/ 2.7 | 3.72 | 55.1 |

[a]Measured in dichloromethane with concentration = 1 × 10⁻⁵ M at room temperature.
[b]Measured in 2-methyltetrahydrofuran at 77K.
[c]The data presented in the parentheses are the difference of the photoluminescence wavelength at room temperature and 77K.
[d]Measured in dichloromethane with concentration = 1 × 10⁻³ M
[e]Measured in THF with concentration = 1 × 10⁻³ M.
[f]HOMO/LUMO levels were determined on the basis of the onset potentials of reduction and oxidation; $E_s$ = HOMO-LUMO.
[g]Phosphorescence lifetime (τ).
[h]5 wt % doped in PMMA at RT.

[a] Measured in dichloromethane with concentration=1× 10⁻⁵ M at room temperature. [b] Measured in 2-methyltetrahydrofuran at 77K. [c] The data presented in the parentheses are the difference of the photoluminescence wavelength at room temperature and 77K. [d] Measured in dichloromethane with concentration=1×10⁻³ M [e] Measured in THF with concentration=1×10⁻³ M. [f] HOMO/ LUMO levels were determined on the basis of the onset potentials of reduction and oxidation; $E_s$=HOMO-LUMO. [g] Phosphorescence lifetime (τ). [h] 5 wt % doped in PMMA at RT.

TABLE 2

Performances of devices B1, B2, G, and R

| Device[a] | $V_{on}$ | $L_{max}$ (cd m⁻²)[b] | $\eta_{ext}$ (%)[c,f] | $\eta_c$ (cd A⁻¹)[d,f] | $\eta_p$ (lm W⁻¹)[e,f] | $\lambda_{max}$ (nm)[g] | C.I.E (x, y)[h] |
|---|---|---|---|---|---|---|---|
| B1 | 3.2 (13.5V) | 20649 | 17.1/ 16.5/ 15.1 | 22.3/ 21.5/ 19.6 | 19.8/ 15.0/ 11.2 | 458 | (0.13, 0.16) |
| B2 | 3.2 (13.5V) | 23727 | 15.4/ 14.3/ 13.6 | 21.9/ 20.4/ 19.3 | 19.1/ 14.2/ 11.0 | 464 | (0.13, 0.18) |
| G | 2.8 (20V) | 74362 | 24.4/ 21.6/ 18.5 | 91.9/ 81.3/ 69.6 | 96.3/ 63.9/ 43.8 | 520 | (0.30, 0.62) |
| R | 3.8 (15.5V) | 16572 | 24.9/ 22.0/ 16.0 | 55.4/ 48.9/ 35.7 | 43.6/ 27.9/ 15.0 | 592 | (0.60, 0.39) |

[a]The cathode of the general device is LiF (1 nm)/Al (100 nm); the structure of devices B1 and B2: ITO/TAPC (50)/t-CzSA (10)/ BCPO: (fpmi)₂Ir(dmpypz) (8%) (Device B1) or BCPO: (mpmi)₂Ir(dmpypz) (8%) (Device B2) (30)/3TPYMB (7)/BPhen (20); device G: ITO/NPB (20)/TCTA (10)/BCPO: (mpmi)₂Ir(pybi) (4%) (30)/BCP (10)/Alq (60); device R: ITO/NPB (10)/TCTA (20)/CBP: (mpmi)₂Ir(priq) (4%) (30)/BCP (20)/Alq (60) and the unit of thickness is nm.
[b]The maximum values of luminance ($L_{max}$).
[c]The external quantum efficiency ($\eta_{ext}$).
[d]The current efficiency ($\eta_c$).
[e]The power efficiency ($\eta_p$).
[f]The efficiencies listed are the maximum value, and the values at 100 and 1000 cd m⁻², respectively.
[g]The maximum values of the wavelength.
[h]Taken at 8 V.

Figure 7:
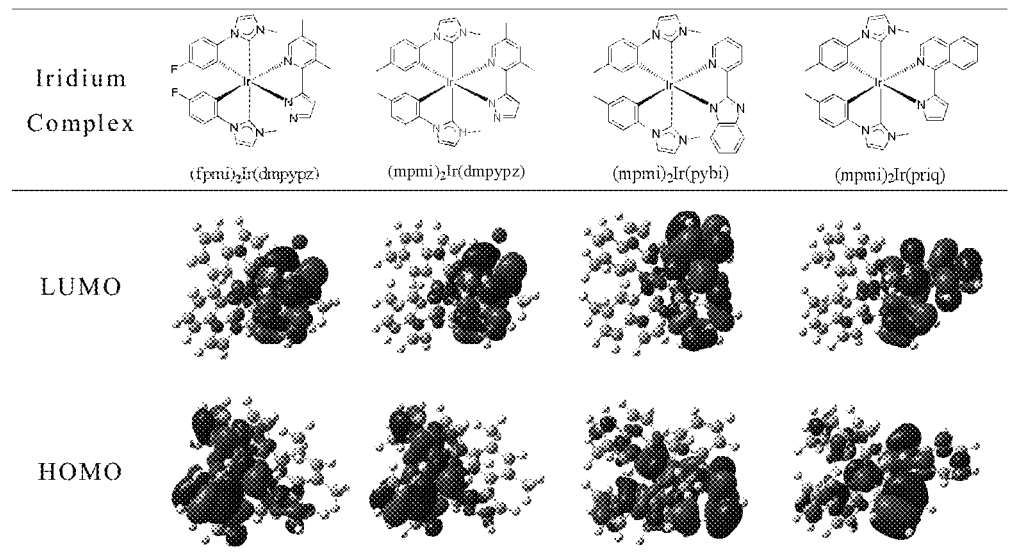
FIG. 7 shows the HOMO and LUMO surfaces of (fpmi)$_2$Ir(dmpypz), (mpmi)$_2$Ir(dmpypz), (mpmi)$_2$Ir(pybi), and (mpmi)$_2$Ir(priq) from DFT calculations.

For (fpmi)₂Ir(dmpypz) and (mpmi)₂Ir(dmpypz), the absorption peaks appearing at 275-320 nm with very large extinction coefficients (ε) of 42000-84000 M⁻¹ cm⁻¹ are assigned as the π-π* transition, while the shoulder near 363 nm (ε≈4000-8000 M⁻¹ cm⁻¹) is likely associated with metal-to-ligand-charge-transfer (MLCT) transitions. For (mpmi)₂ Ir(pybi) and (mpmi)₂Ir(priq), the π-π* transitions appear at 301-358 nm (ε≈39000-43000 M⁻¹ cm⁻¹) and 272-420 nm (ε≈38000-59000 M⁻¹ cm⁻¹), respectively. Besides, the absorptions around 401 nm (ε≈7000 M⁻¹ cm⁻¹) and 488 nm (ε≈1200 M⁻¹ cm⁻¹) are assigned as the MLCT transitions of (mpmi)₂Ir(pybi) and (mpmi)₂Ir(priq), respectively. A close comparison of the emission wavelengths and colors with the structures of these iridium complexes reveals the key feature of these complexes. As shown in Table 1, the emission maxima of (fpmi)$_2$Ir(dmpypz), (mpmi)$_2$Ir(dmpypz), (mpmi)$_2$ Ir(pybi) and (mpmi)$_2$Ir(priq) appear at 455, 466, 530, 599 nm, respectively. For (fpmi)$_2$Ir(dmpypz) and (mpmi)$_2$Ir(dmpypz) in which the biscarbene ligands are different, the emission maxima changes only by 11 nm. In contrast, for (mpmi)$_2$Ir(dmpypz), (mpmi)$_2$Ir(pybi) and (mpmi)$_2$Ir(priq) with the same biscarbene ligands, but different N^N ligands, the emission colors and wavelengths alter greatly. The colors change from blue to green and to red, and the wavelengths vary by 133 nm. This result demonstrated that the heteroleptic N^N ligands play a very important role for the control of the emission color. Molecular orbital calculations of these four iridium complexes (see FIG. 7) show that the LUMOs of these complexes are all located on the N^N ligands, while the HOMOs are dispersed on the metal center, and the C^C and the N^N ligands. These results provide the basis that the N^N ligands play a key factor in the emission color of these iridium complexes.

Figure 8:
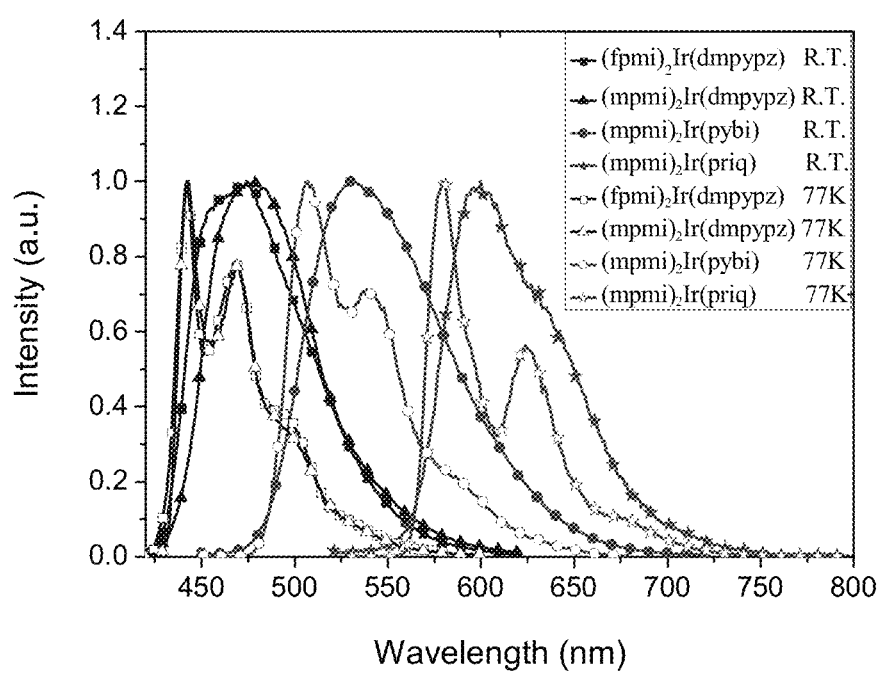
FIG. 8 shows the photoluminescence spectra of iridium biscarbene complexes at room temperature and 77K.

The emission spectra of these complexes at different temperature shows that the emission maxima are blue-shifted by ca. 13-23 nm in 2-methyltetrahydrofuran at 77 K relative to those in dichloromethane at room temperature (see FIG. 8). In light of the apparent rigidochromic shift without fine vibronic progression of the emission spectra at 77 K, we speculate that a significant MLCT character is involved in the excited state of heteroleptic complexes at room temperature. The triplet phosphorescence lifetimes (I) of these iridium biscarbene complexes were also measured by intensified charge coupled device (ICCD) camera and are listed in Table 1. The observed large blue-shift of emission spectra at 77 K and the short phosphorescent life-times suggest that these four triplet emitters should possess good emission efficiency.

Figure 9:
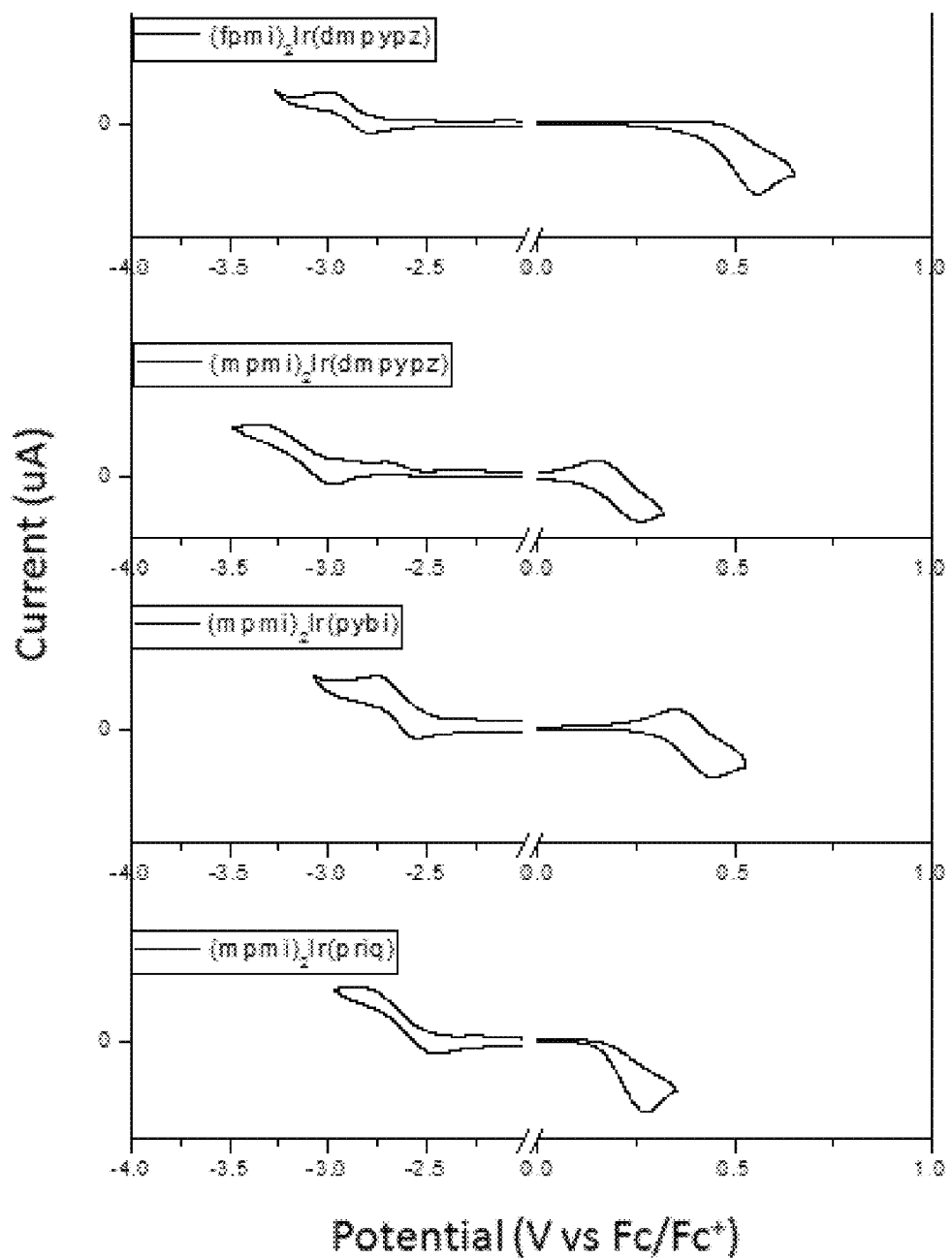
FIG. 9 shows the cyclic voltammograms of (fpmi)$_2$Ir(dmpypz), (mpmi)$_2$Ir(dmpypz), (mpmi)$_2$Ir(pybi), and (mpmi)$_2$Ir(priq)

The electrochemical behaviors of these heteroleptic iridium complexes were investigated by cyclic voltammetry (see FIG. 9). The measured onset oxidation and reduction potentials of each complex were used to calculate the HOMO and LUMO levels, respectively. As listed in Table 1, the HOMO/LUMO levels of (fpmi)$_2$Ir(dmpypz), (mpmi)$_2$Ir(dmpypz), (mpmi)$_2$Ir(pybi), and (mpmi)$_2$Ir(priq) are 5.2/2.0, 5.1/1.9, 5.1/2.3, and 5.0/2.3 eV, respectively. The calculated energy gaps based on these oxidation and reduction potentials agree well with the observed blue, green and red emission spectra of these complexes. Because of the electron-withdrawing ability of the fluoro group in ligand fpmi, (fpmi)$_2$Ir(dmpypz) showed lower HOMO levels of 5.2 eV relative to (mpmi)$_2$Ir(dmpypz).

Figure 10:
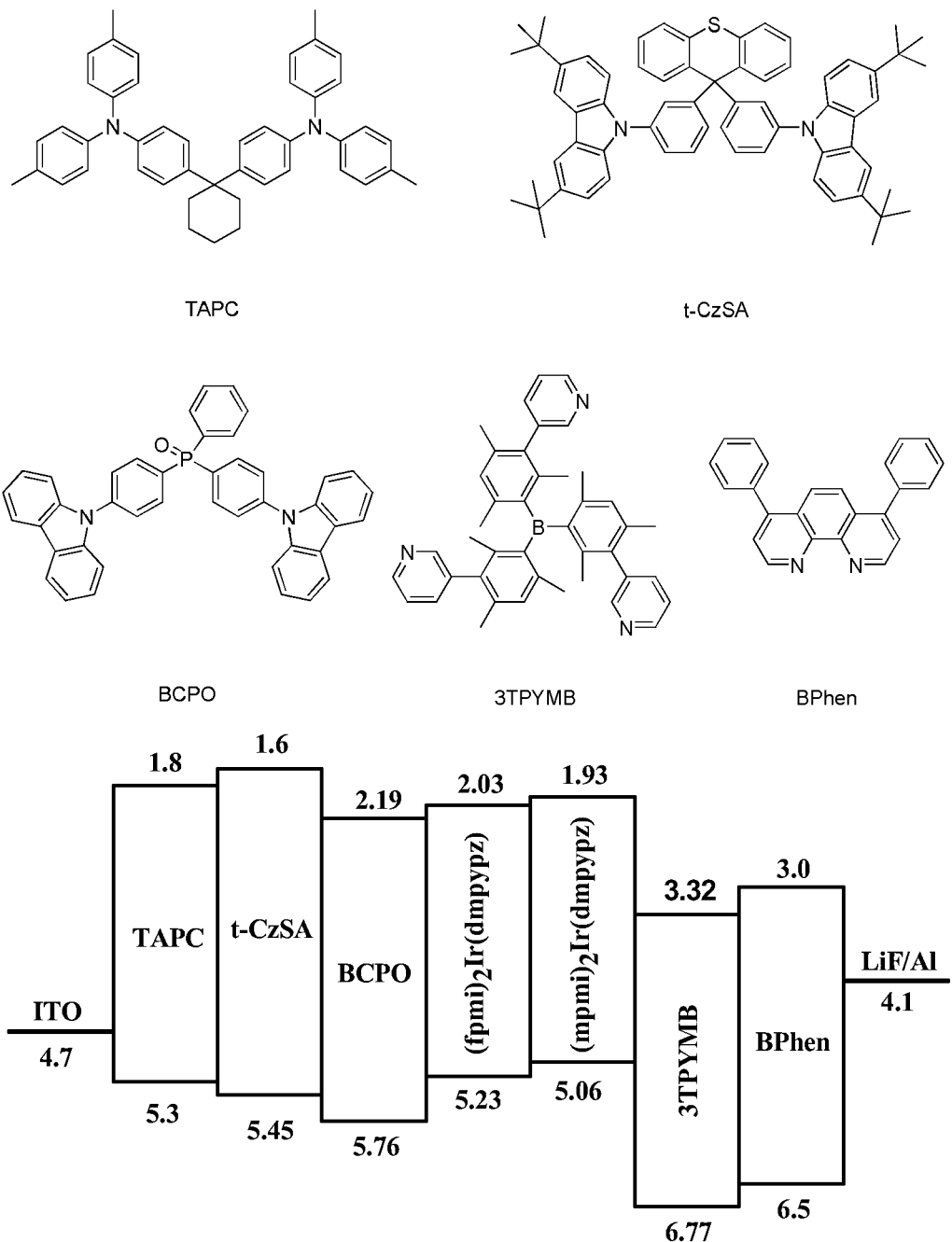
FIG. 10 shows the chemical structures and energy levels of the materials used for blue devices.

To understand the electroluminescent properties of these complexes, we fabricated four devices B1, B2, G and R, using these heteroleptic iridium biscarbene complexes as the dopant emitters. In device B1, BCPO (bis-4-(N-carbazolyl) phenyl)phenylphosphine oxide) is used as the host material and (fpmi)$_2$Ir(dmpypz) as the dopant emitter. The device structure consists of the following layers: ITO (indium tin oxide)/TAPC (50 nm)/t-CzSA (10 nm)/BCPO: (fpmi)$_2$Ir(dmpypz) (8%) (30 nm)/3TPYMB (7 nm)/BPhen (20 nm)/LiF (1 nm)/Al (100 nm), where TAPC (1,1-bis(4-(N,N'-di(p-tolyl)amino)phenyl)cyclohexane) is served as a hole injection layer and t-CzSA (9,9'-(3,3'-(9H-thioxanthene-9,9-diyl)bis(3,1-phenylene))bis(3,6-di-tert-butyl-9H-carbazole)) is the hole transporting and exciton blocking layer, respectively. The thin layer of 3TPYMB (tris(2,4,6-trimethyl-3-(pyridin-3-yl)phenyl)borane) is used as the exciton blocking layer, while BPhen (4,7-diphenyl-1,10-phenanthroline) and LiF act as the electron transporting and injection layers (see FIG. 10). Device B2 was fabricated similarly, except that (mpmi)$_2$Ir(dmpypz) (8%) was employed as the dopant. Devices B1 and B2 showed maxima EQEs of 17.1 and 15.4%, maxima luminance of 20649 and 23727 cd m$^{-2}$, maxima current efficiencies of 22.3 and 21.9 cd A$^{-1}$ and maxima power efficiencies of 19.8 lm W-1 and 19.1 lm W$^{-1}$ with CIE coordinates of (0.13, 0.16) and (0.13, 0.18), respectively. At high brightness of 1000 cd m$^{-2}$, the external quantum efficiency of devices B1 and B2 still maintain as high as 15.1% and 13.6%, respectively. Both devices show very low efficiency roll-off value of 11.7%. Compared with the deep blue phosphorescence devices reported, the EQEs of these two devices 1000 cdm$^{-2}$ appear to be the highest ones. In particular, device B1 shows the highest luminance and lowest efficiency roll-off of the deep-blue phosphorescence devices with CIE$_{x+y}$<0.30.

Figure 11:
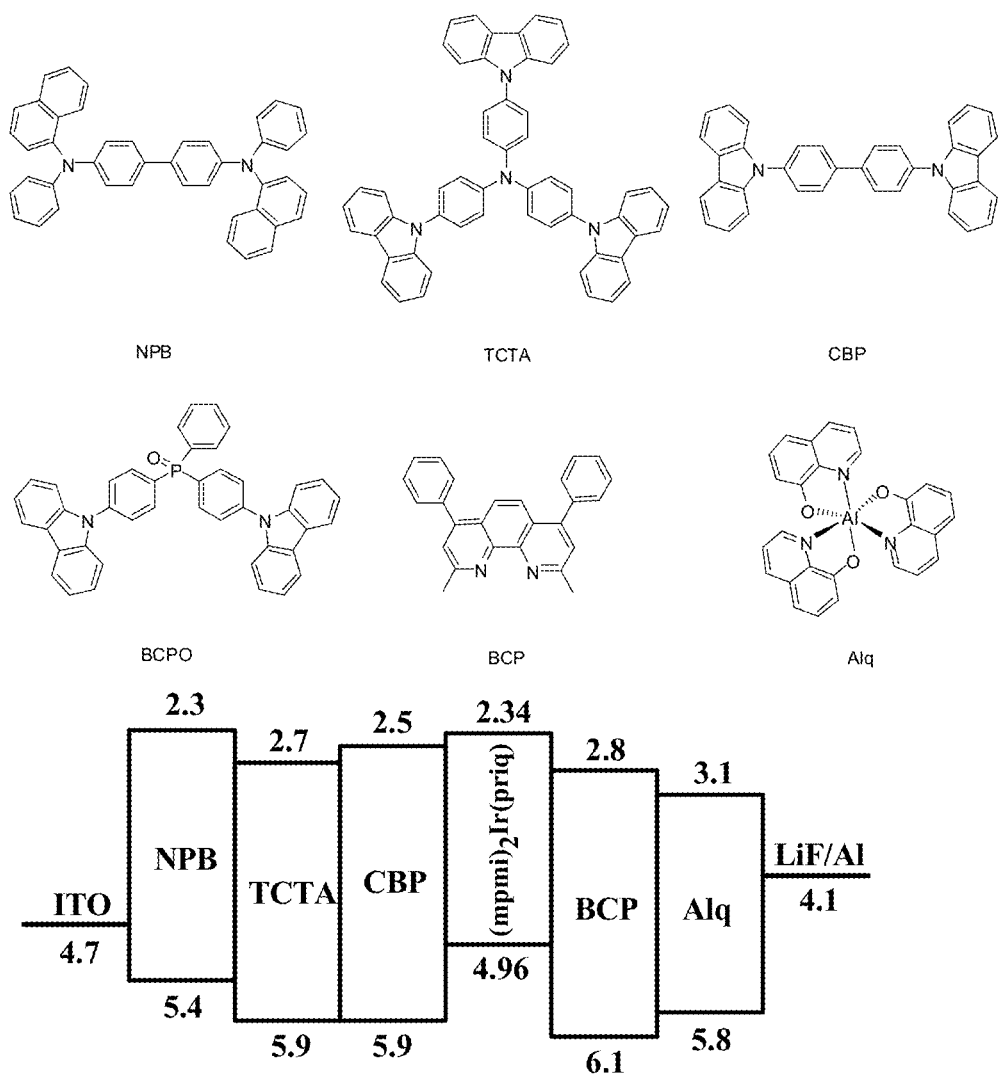
FIG. 11 shows the chemical structures and energy levels of the materials used in green and red devices.
Figure 11:
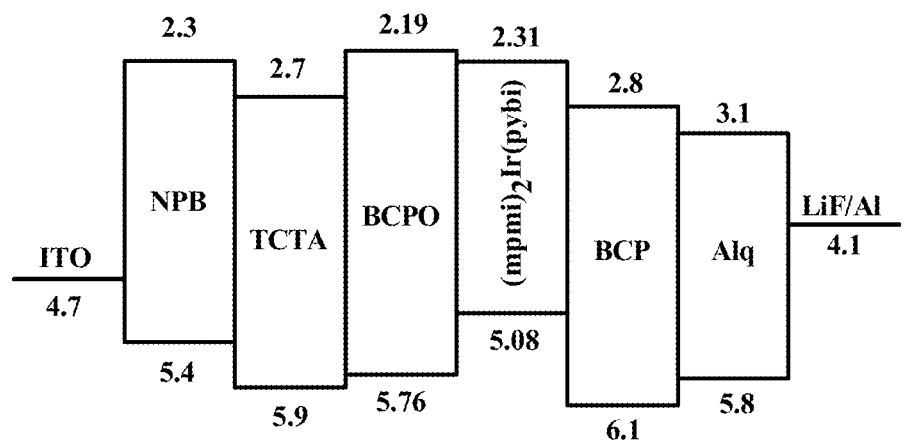

Device G also uses BCPO as the host material, but employs (mpmi)$_2$Ir(pybi) as the dopant emitter. The device configuration consists of ITO/NPB (20 nm)/TCTA (10 nm)/BCPO: (mpmi)$_2$Ir(pybi) (4%) (30 nm)/BCP (10 nm)/Alq (60 nm)/LiF (1 nm)/Al (100 nm), where NPB (N,N'-bis(naphthalen-1-yl)-N,N'-bis(phenyl)benzidine) and TCTA (4,4',4"-tris(carbazol-9-yl)-triphenylamine) serve as the hole injection and transport layers, respectively; BCP (2,9-dimethyl-4,7-diphenyl-1,10-phenanthroline) and Alq (tris(8-hydroxyquinolinato)aluminum) serve as a hole blocking layer and electron transporting layer, respectively (see FIG. 11). Device G emits green light with CIE coordinates of (0.30, 0.62) very efficiently. An extremely high external quantum efficiency of 24.4%, current efficiency of 91.9 cd A$^{-1}$, power efficiency of 96.3 lm W$^{-1}$, and maximum brightness of 74362 cd m$^{-2}$ were observed. Device R based on (mpmi)$_2$Ir(priq) as the dopant emitter consists of the following layers: ITO/NPB (10 nm)/TCTA (20 nm)/CBP: (mpmi)$_2$Ir(priq) (4%) (30 nm)/BCP (20 nm)/Alq (60 nm)/LiF (1 nm)/Al (100 nm), where CBP=4,4'-di(9H-carbazol-9-yl)-1,1'-biphenyl. The device gives red emission with CIE coordinates of (0.60, 0.39). Furthermore, it reveals an extremely high external quantum efficiency of 24.9%, current efficiency of 55.4 cd A$^{-1}$, power efficiency of 43.6 lm W$^{-1}$, and maximum brightness of 16572 cd m$^{-2}$. While very high efficient green and red devices were reported recently, both devices G and R are among the highest ones that are known to date. The observed extremely high efficiencies of these iridium complexes-based devices provide an alternative choice for phosphorescent dopant emitters in the OLEDs other than the well-known iridium C^N complexes.

In summary, this invention discloses transition metal carbene complex and the luminescent application thereof. The transition metal carbene complex can give deep-blue, green, and red phosphorescent emission by the choice of different heteroleptic N^N ligands. It is the first time that the emission energy of iridium biscarbene complexes can be tuned over a wide range from 455 to 599 nm. The devices using (fpmi)$_2$Ir(dmpypz), (mpmi)$_2$Ir(dmpypz), (mpmi)$_2$Ir(pybi) and (mpmi)$_2$Ir(priq) as dopant emitters showed excellent external quantum efficiencies of 17.1, 15.4, 24.4 and 24.9% with CIE coordinates of (0.13, 0.16), (0.13, 0.18), (0.30, 0.62) and (0.60, 0.39), respectively. Therefore, according to this invention, a luminescent device can display wide-range color tuning ability with high luminescent efficiency.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A transition metal carbene complex, represented by the following formula:

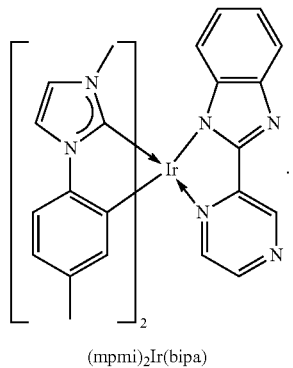

(mpmi)₂Ir(bipa)

2. An electroluminescent device, comprising a pair of electrodes and at least one organic layer disposed between said electrodes, said at least one organic layer comprises an emitting layer and a transition metal carbene complex, wherein said transition metal carbene complex is represented by the following formula:

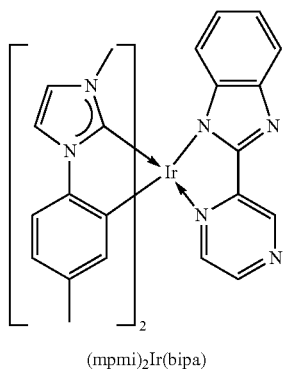

(mpmi)₂Ir(bipa)

* * * * *